United States Patent [19]
Cross, Jr.

[11] Patent Number: 5,843,146
[45] Date of Patent: Dec. 1, 1998

[54] ADJUSTABLE MEDICAL LEAD ANCHOR

[75] Inventor: Thomas E. Cross, Jr., St. Francis, Minn.

[73] Assignee: Medtronic Incorporated, Minneapolis, Minn.

[21] Appl. No.: 846,806

[22] Filed: Apr. 30, 1997

[51] Int. Cl.⁶ .......................... A61M 25/02; A61M 25/01
[52] U.S. Cl. ............................ 607/115; 607/117; 604/174
[58] Field of Search ..................................... 607/115, 116, 607/117, 149; 604/174, 175, 179

[56] References Cited

U.S. PATENT DOCUMENTS

| | | | |
|---|---|---|---|
| 5,058,584 | 10/1991 | Bourgeois | 128/421 |
| 5,152,298 | 10/1992 | Kreyenhagen et al. | 607/116 |
| 5,273,053 | 12/1993 | Pohndorf | 604/175 |
| 5,476,493 | 12/1995 | Muff . | |
| 5,632,729 | 5/1997 | Cai et al. . | |
| 5,683,446 | 11/1997 | Gates . | |

*Primary Examiner*—William E. Kamm
*Assistant Examiner*—Carl H. Layno
*Attorney, Agent, or Firm*—Banner & Witcoff Ltd

[57] ABSTRACT

A medical lead anchor anchors a medical lead relative to the epidural space of the spinal cord, intrathecal space, or peripheral nerve of a patient. The lead anchor comprises a sleeve having a plurality of eyelets and a passage through the sleeve. The anchor further comprises a locking device defining a collet, a collet driver and a handle. The locking device has a lead passage. The collet driver is sized to fit the passage in the sleeve and has a spiral slot to operatively engage a pin on the sleeve located in the sleeve passage. The sleeve and attached locking device are slid over the lead. The sleeve is sutured to tissue located near the location where the lead enters the epidural space. The collet and collet driver of the locking device are moved along the passage of the sleeve with the spiral slot of the collet driver operatively engaging the pin. The handle of the locking device is turned, moving the collet and collet drive as described, to advance the collet through the passage in the sleeve, thereby pinching the collet to a pre-determined tightness on the lead and thus releasably securing the lead in the desired position.

21 Claims, 2 Drawing Sheets

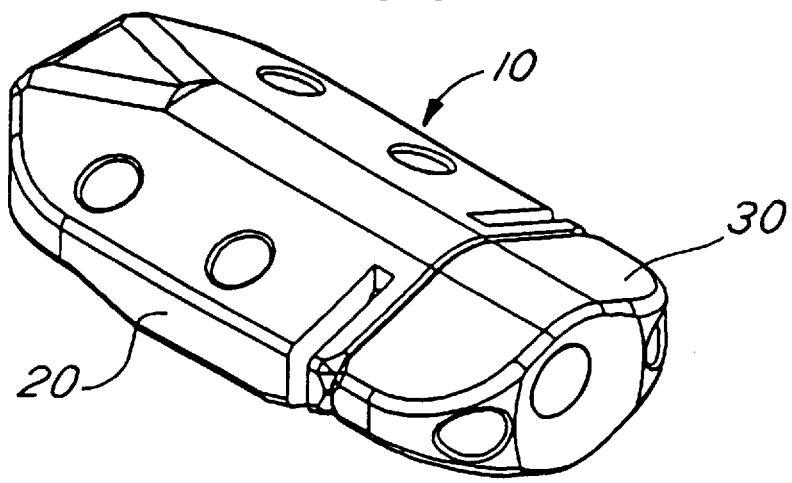
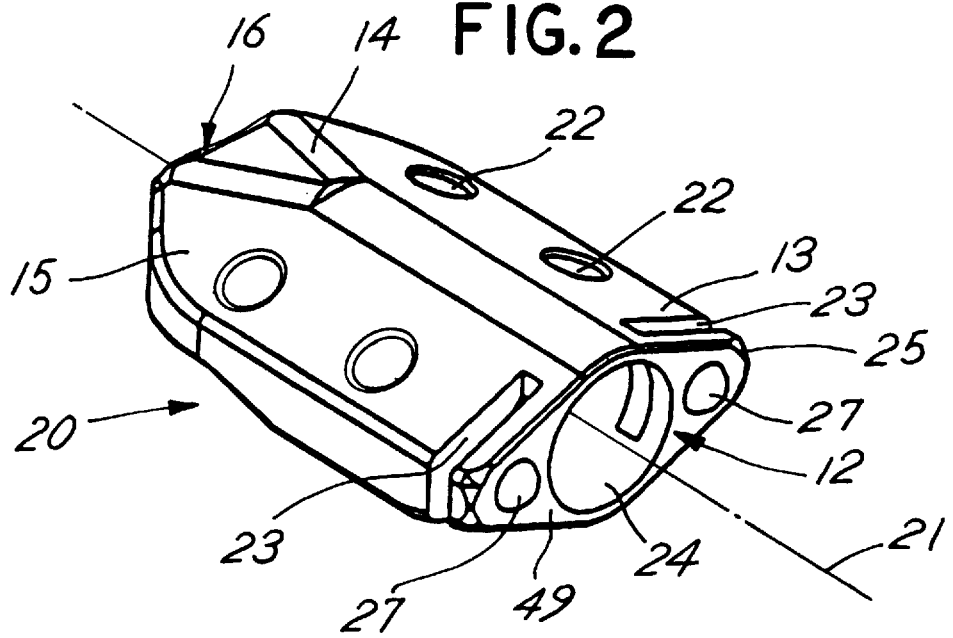

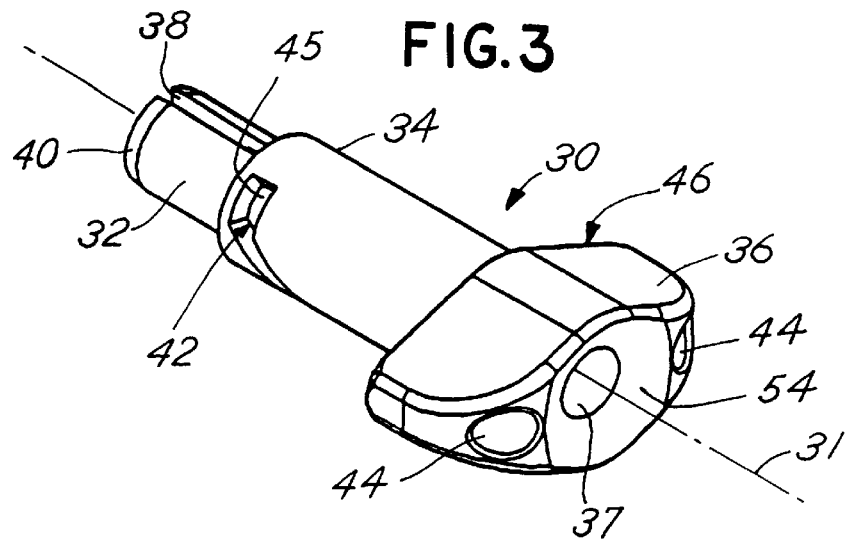
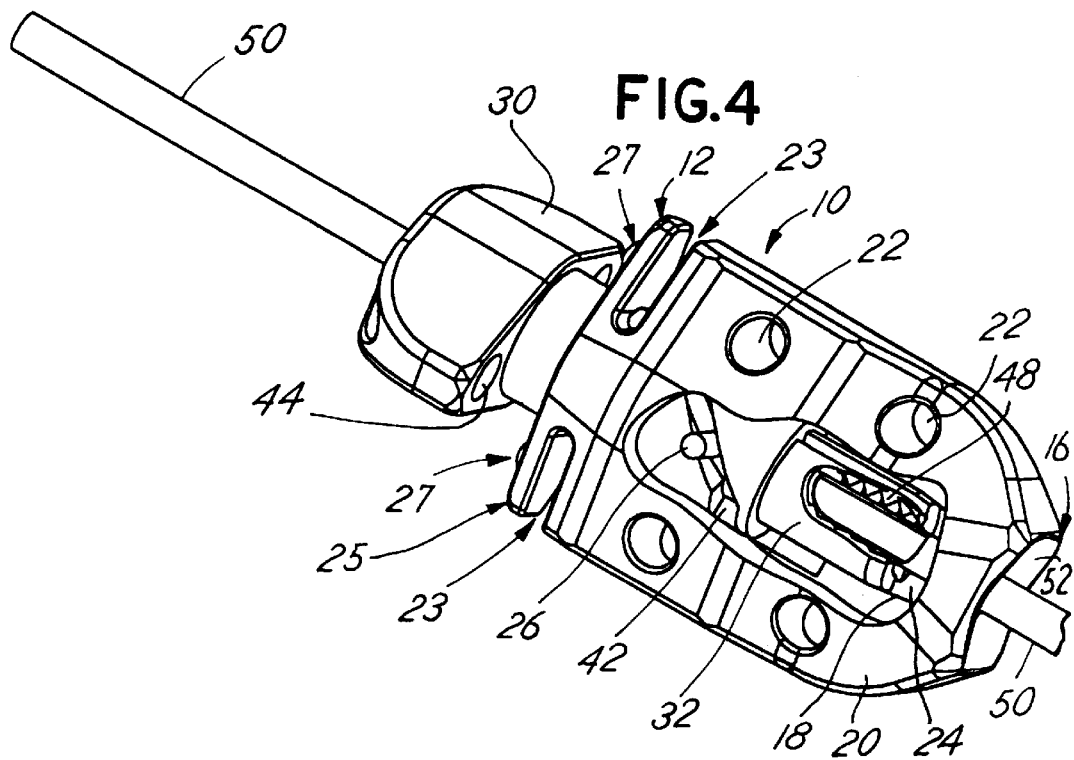

ADJUSTABLE MEDICAL LEAD ANCHOR

BACKGROUND OF THE INVENTION

1. Field of the Invention

This invention relates generally to the techniques for delivering electrical stimulation and medication to the spinal cord and the cerebrospinal fluid that bathes the spinal cord. Specifically, this invention relates to an apparatus for securing and repositioning a stimulation or medication delivering lead after the lead is positioned in the spinal epidural space, the intrathecal space or in a peripheral nerve application. Moreover, this invention relates to an apparatus for securing and repositioning a medication delivering catheter after the catheter is positioned in the intrathecal space.

2. Description of the Related Art

Electrical stimulation and medication delivery to the spinal cord and cerebrospinal fluid are usefull in treating intractable malignant and nonmalignant pain, and severe spasticity associated with multiple sclerosis, spinal cord injury, cerebral palsy, and traumatic brain injury. A patent of interest it issued to Bourgeois, U.S. Pat. No. 5,058,584, illustrates the use of an implantable pulse generator and lead to inject bursts of high frequency stimulation into the epidural space. Through the use of an implantable, programmable pump and lead, precise drug doses can be directly delivered to the cerebrospinal fluid to help relieve chronic pain or severe spasticity.

Controlled placement of drug delivering catheters in the intrathecal space or controlled placement of leads in the epidural space, intrathecal space, or in peripheral nerve applications is highly desirable. Precision in placement may lead to improved treatment, as drugs and stimulation are released at the point or points at which treatment causes maximum beneficial effects. Physicians desire controlled placement for these reasons. When implanting an epidural lead, a physician must surgically open the human body to the epidural space, and then insert the lead into the epidural space to the desired location. Fluoroscopy aids the physician, and trial and error tests of treatment define the desired location(s) for treatment. At present, in attempts to secure leads or catheters, physicians suture sleeves on the leads or catheters to surrounding tissue where the leads enter the epidural space or catheters enter the intrathecal space. The sleeves require sutures to prevent movement between the sleeve and lead. The quality of the connection between the sleeve and lead depends on the tightness of the sutures and is highly variable. Further, the leads and catheters frequently need to be repositioned. Known sleeves require physicians to remove the sutures before any repositioning is possible. As a result, a less than optimal placement is not easily made optimal, or an initially optimal placement readjusted as over the passage of time, the placement becomes less than optimal. And if sutures are removed, a physician must re-suture the sleeve to surrounding tissue.

SUMMARY OF THE INVENTION

The present invention recognizes and provides a solution to the problems of lead or catheter placement in providing a unique lead anchor that allows rapid, accurate and secure positioning and repositioning of leads or catheters.

Accordingly, an object of the present invention is to provide a unique medical lead anchor that anchors an epidural lead or intrathecal catheter and allows the lead or catheter to be readily, securely positioned and repositioned as desired. Another object of the invention is to provide a lead anchor that need only be sutured to surrounding tissue once, with repositioning remaining possible.

The present invention provides a lead anchor for securing and repositioning a lead in the epidural space of the human spinal cord, in the intrathecal space or in a peripheral nerve application. Moreover, the present invention provides a lead anchor for securing and repositioning a drug it delivering catheter in the intrathecal space. The present invention comprises, in the preferred embodiment, a sleeve and a locking device. The sleeve has a plurality of eyelets for suturing the sleeve to surrounding tissue. A passage extends through the sleeve. The locking device includes a collet, a collet driver, and a handle. A lead passage extends through the locking device. The collet driver is sized to fit the passage in the sleeve and has a recessed spiral slot. A pin is fixed to the sleeve and engages the spiral slot in the collet driver.

In use, when the epidural lead is desirably positioned into the spinal epidural space, or when the catheter is desirably positioned into the intrathecal space, the lead anchor is slid along the lead or catheter to the tissue adjacent the opening to the epidural space or intrathecal space. The sleeve is sutured through its eyelets to surrounding tissue. The locking device is then turned with respect to the sleeve. The pin operatively engages the spiral slot of the collet driver, and as the handle of the locking device is turned by hand, the engagement of the pin and the spiral slot advances the collet driver and the collet. The collet is pinched at a taper within the passage of the sleeve, between the sleeve and lead or catheter, resulting in a pre-determined tightness, or gripping, or wedging of the collet on the lead or catheter and a controlled securement of the lead or catheter in its desired position.

Advantageously, if the lead or catheter needs to be repositioned, the physician may simply turn the handle of the locking device opposite the direction used for tightening, to release the lead or catheter from the collet and allow the physician to reposition the lead or catheter with respect to the lead anchor. After repositioning, the physician may simply re-turn the handle of the locking device and re-secure the lead or catheter. Thus, the present invention eliminates the removal of sutures for longitudinal repositioning of an epidural lead.

BRIEF DESCRIPTION OF TIE DRAWING

The preferred embodiment of the invention is illustrated in the drawing, wherein like reference numerals refer to like elements in the various views, and wherein:

FIG. 1 is a perspective view of the preferred lead anchor assembly of the present invention.

FIG. 2 is a perspective view of the preferred lead anchor sleeve of the present invention.

FIG. 3 is a perspective view of the preferred lead anchor locking device of the present invention.

FIG. 4 is a perspective view of the assembly of FIGS. 2–3 in situ with a portion of the lead anchor sleeve removed to illustrate the engagement of the lead anchor locking device with the lead anchor sleeve.

DETAILED DESCRIPTION OF THE PREFERRED EMBODIMENT

Referring to FIG. 1, a preferred embodiment of the medical lead anchor 10 of the invention comprises a shell or sleeve 20 and a lead-interactive fastener or locking device 30, both preferably molded of polysulfone or other suitable material.

Referring to FIG. 2, the preferred sleeve 20 is symmetrical about a longitudinal centerline 21. The preferred sleeve 20 is generally rectangular in plan view, with a width approximately half its length. The sleeve 20 defines a plurality of eyelets 22 and a passage 24. The passage 24 is generally circular and uniform in cross-section, and extends centrally through the sleeve 20. The passage 24 is centered on the longitudinal centerline 21 of the sleeve 20. Externally, the sleeve 20 tapers in thickness laterally from a central thickness greater then the greatest diameter of the passage 24. A proximal end 12 of the sleeve is flat and lies in a transverse plane. A proximal portion 13 is generally uniform in cross-section throughout its length. Domed members or protuberances or buttons 27 protrude longitudinally outward from the flat proximal end 12. A distal portion 15 narrows in width along slanted surfaces 14 to a narrowed, distal end 16.

Referring to FIGS. 1 and 4, the passage 24 extends outward through both ends 12, 16 of the sleeve 20, and ends in an inward, gradual taper 18 (FIG. 4) at and toward the distal end 16. At the smallest diameter of the taper, as elsewhere, the passage 24 has a diameter sufficient for the lead or catheter 50 to pass through the passage 24.

The eyelets 22 are spaced from the passage 24, and extend generally perpendicular to a transverse plane through the sleeve 20.

The sleeve 20 further defines transversely extending slots 23 between the sleeve body and adjacent transversely extending wings or cantilevers or bending beam members 25. The members 25 are flexible in arcuate paths about the bases of the members 25, toward and narrowing of the slots 23, as will be explained. Except as to passage 24, eyelets 22, and slots 23, the sleeve 20 is a solid body.

Referring to FIG. 3, the locking device or member 30 includes a collet 32, a collet driver 34, and a handle member 36. These members are joined in series longitudinally along an axis 31. Preferably, they are molded as a single piece. When the locking device 30 is assembled with the sleeve 20, the axis 31 is co-axial with the centerline 21.

The locking device 30 has a lead passage 37 through the locking device 30 along the axis 31. The lead or catheter 50 fits through the lead passage 37. In contrast, the locking device 30 fits through the sleeve passage 24.

The collet 32 is annular, with at least one slit 38 that runs parallel to the centerline of the collet, with a tapered end 40. The collet 32 is fixed to the collet driver 34. Referring to FIG. 4, the collet 32 has an internal grip in the form of an internally threaded portion 48 for gripping the lead or catheter 50. The internally threaded portion 48 may also be in the form of a lip or bump, as will be described.

Referring again to FIG. 3, the collet driver 34 is annular, has a shallow, recessed spiral slot 42 along its exterior, and is sized to fit the sleeve passage 24 in the sleeve 20. Referencing FIG. 4, a pin 26 is located on the inner cylindrical wall of the passage 24 of the sleeve 20 and juts radially into the passage 24. The pin 26 is press fit into a hole on the side of the sleeve 20. The pin hole is not shown, as the pin hole is defined in the side of the sleeve shown in FIG. 4, where the sleeve 20 is broken away to reveal detail. The pin 26 is press fit in the pin hole during manufacture when any portion of the spiral slot 42 in the collect driver 34 is aligned with the pin hole. The spiral slot 42 of the collet driver 34 is sized to mate the pin 26 and extends to an arcuate slot section 45 generally perpendicular to the centerline of the collet driver 34.

The collet driver 34 is fixed to the handle member 36. The member 36 has external surfaces for contact by surgeon's fingers, and for rotation about the axis 31 when so urged. The member 36 has longitudinally extending openings 44 for holding the locking device 30 to the sleeve 20. The openings mate with the domed buttons 27, as will be described. A distal face 46 of the handle portion 36 is flat, to complement the proximal face 49 of the proximal end 12 of the sleeve 20. As in FIG. 1, the outer side surfaces of the locking device handle portion 36 match and merge into those of the sleeve 20, when the handle portion 36 and sleeve 20 are aligned.

Leads are typically manufactured to specifications including the minimum radius about which the leads must bend without permanent change in shape, kinking or fracture. Where the lead or catheter 50 exits the lead anchor 10, at both the sleeve 20 and the locking member 30, and as referenced at 52 and 54 in FIGS. 3 and 4, damage resistant faces of the lead anchor are contoured to limit lead bending relative to the lead anchor 10 to no less than the minimum radius of the lead specifications. As an example, faces 52, 54 are contoured to limit lead bending relative to the lead anchor to a radius of no less than 3 millimeters.

In use, the sleeve 20 and locking member 30 are threaded on the lead or catheter 50 as a unit. The distal ends of the sleeve 20 and locking member 30 are oriented toward the patient, i.e., toward the opening to the epidural space. After the lead or catheter 50 is properly positioned in the epidural space or the intrathecal space, the lead anchor 10 is slid along the lead or catheter 50 so that the distal end 16 of the sleeve 20 is adjacent the location where the lead 50 enters the epidural space. The sleeve 20 is then sutured to surrounding human tissue through the eyelets 22. The locking device 30 is turned relative to the sleeve 20. The pin 26 operatively engages the spiral slot 42 of the collet driver 34. As the handle portion 36 of the locking device 30 is turned by hand, the engagement of the pin 26 and the spiral slot 42 advances the collet 32 in the passage 24. The collet 32 is pinched against and within the taper of the passage 24 of the sleeve 20, between the sleeve 20 and lead or catheter 50, resulting in a pre-determined tightness of the collet 32 and the lead anchor 10 on the lead or catheter 50. The grip in the form of the internal thread 48 grips the lead or catheter 50 resulting in a controlled and releasable securement of the lead or catheter 50 in its desired position. The grip may also be accomplished with an internal bump or lip for releasable securement of the lead 50.

As the collet 32 reaches the gripping position, the handle portion of the locking device 30 reaches alignment with the sleeve 20. The domed buttons 27 contact the face 46 of the handle portion 36. Contact causes the bending members 25 to bend arcuately in the distal direction, storing restorative energy. In the gripping position of the collet, the buttons 27 simultaneously drop into the openings 44 in the handle portion 36 of the locking device 30, as the pin 26 reaches the non-spiral portion of the otherwise spiral slot 42. The bending members 25 return to their unbent positions, under action of the restorative force. The fit of the buttons 27 into the openings 44 retains the buttons 27 in the openings 44, and thereby retains the locking device 30 aligned with and locked to the sleeve 20. Thus, under continuing gripping by the grip, the lead 50 is fastened to the anchor 10 against movement relative to the anchor 10 and thereby relative to the human tissue and epidural space.

If the lead or catheter 50 needs to be repositioned, the physician simply turns the handle portion 36 opposite the direction used for locking, to release the lead 50 from the collet 32 and allow the physician to reposition the lead 50. As the buttons 27 contact the sidewalls of the button openings 44, the bending members 25 bend toward the slots 23, allowing the buttons to rise from the openings. The locking device 30 is released from the sleeve 20.

In an alternative phrasing used to more completely explain the concepts of the invention, the medical lead anchor 10 defines a first body 20 and a second body 30 which together define a first-and-second-body-interactive lead-interactive fastener, whereby interaction of the second body 30 with the first body 20 causes fastening of the lead or catheter 50 to the anchor 10. Alternatively, the first body 20 and the second body 30 have movement-interactive members, perhaps in the form of the bending members, buttons, and cooperating openings of the preferred embodiment, whereby movement of the second body 30 relative to the first body 20 causes fastening of the lead or catheter 50 to the anchor 10. In another phrasing, the second body 30 defines a second sleeve 37 for the lead 50, whereby the lead may be placed through the second sleeve 37 and the second body 30 may be moved along the lead or catheter 50 to the first body 20. In yet another phrasing, the collet 32 defines a wedge 48, in the form of the collet and the sleeve passageway taper, or otherwise, whereby movement of the locking device 30 relative to the sleeve 20 wedges the wedge 48 against the lead 50.

Because the complementary relationship of the exteriors of the locking device and sleeve, and because of the shapes of the locking device and sleeve themselves, the locking device is chronically implantable without substantial risk to patients.

Those of ordinary skill in the art will recognize that modifications can be made to the lead anchor described herein without departure from the true spirit and scope of the invention. For example, the collet 32, the collet driver 34 and handle portion 36 do not need to be molded as a unit for the present invention. As another example, alternate tissue-fixation members, such as perhaps tissue barbs extending from the sleeve, could be substituted for sutures and the suture eyelets, which are themselves a form of tissue-fixation members. As yet another example, the button or detent openings 44 of the handle 36 need not be through holes. They may be blind holes or generally, inclusive of through holes, recesses, in the face 46 of the handle 36.

The true spirit and scope of the inventions of this specification are best defined by the appended claims, to be interpreted in light of the foregoing specification. Therefore, to particularly point out and distinctly claim the subject matter regarded as invention, the following claims conclude this specification.

I claim:

1. A medical lead anchor, for anchoring a lead relative to the epidural space of a human spinal cord, the anchor having a body defining a lead fitting, at least one tissue fixation member, and a lead-interactive fastener defining a collet, whereby the body is fitted to the lead and fastened to human tissue adjacent the epidural space using the tissue fixation member, and the lead is fastened to the anchor against movement relative to the anchor and thereby relative to the human tissue and epidural space.

2. A medical lead anchor as in claim 1, the anchor having multiple eyelets for multiple fastening to human tissue.

3. A medical lead anchor as in claim 1, the body including a sleeve for the lead, whereby the lead is placed through the sleeve and the body is moved along the lead into position relative to the human tissue.

4. A medical lead anchor as in claim 1, having a second body, the second body and the first body together defining a first-and-second-body-interactive lead-interactive fastener, whereby interaction of the second body with the first body causes fastening of the lead to the anchor.

5. A medical lead anchor as in claim 4, the first body and the second body having movement-interactive members, whereby movement of the second body relative to the first body causes fastening of the lead to the anchor.

6. A medical lead anchor as in claim 5, the second body defining a second sleeve for the lead, whereby the lead is placed through the second sleeve and the second body is moved along the lead to the first body.

7. A medical lead anchor as in claim 5, the movement interactive members including a wedge, whereby movement of the first body and the second body relative to each other wedges the wedge against the lead.

8. A medical lead anchor, for anchoring a lead relative to the epidural space of a human spinal cord, the anchor comprising:
   a body defining a lead fitting, and at least one eyelet; and
   a second body and a lead-interactive fastener defining a collet, whereby the body is fitted to the lead and fastened to human tissue adjacent the epidural space using the eyelet, and the lead is fastened to the anchor against movement relative to the anchor and thereby relative to the human tissue and epidural space.

9. A medical lead anchor for securing and repositioning a lead in the epidural space of the spinal cord comprising:
   a sleeve defining at least one eyelet, and a passage through the sleeve, and
   a locking device defining a collet, a collet driver, and a handle portion, whereby the sleeve is fitted to the lead and fastened to human tissue adjacent the epidural space using the eyelet, and the lead is fastened to the anchor using the locking device against movement relative to the anchor and thereby relative to the human tissue and epidural space.

10. The medical lead anchor as in claim 9, wherein the collet driver of the locking device is sized to engage the passage through the sleeve, whereby interaction of the sleeve with the locking device causes fastening of the lead to the anchor.

11. The medical lead anchor as in claim 9, wherein the sleeve has multiple eyelets for multiple fastening to human tissue.

12. The medical lead anchor as in claim 9, wherein the passage through the sleeve includes a taper.

13. The medical lead anchor as in claim 9, wherein the locking device has a centerline and a lead passage through the locking device.

14. The medical lead anchor as in claim 13, wherein the collet of the locking device has at least one slit substantially parallel to the centerline of the locking device and a tapered end.

15. A medical lead anchor for securing and as needed repositioning a lead in the epidural space of the spinal cord comprising:
   a sleeve having a plurality of eyelets, and a passage through the sleeve, and
   a locking device having a collet, a collet driver, and a rotary handle, and defining a centerline and a lead passage through the locking device, the collet driver sized to engage the passage through the sleeve and having a spiral slot,
   the locking device pinned to the sleeve along the spiral slot,
   whereby the lead anchor is fitted to the lead, the sleeve fastened to human tissue adjacent the epidural space using the plurality of eyelets, the locking device rotated by manipulation of the rotary handle, rotation driving the locking device along the centerline wedging the collet in the passage against the lead, and thereby the lead is releasably fastened to the lead anchor, and further thereby relative to the human tissue and epidural space.

16. The medical lead anchor as in claim 15, wherein the sleeve has a pin located within the passage, whereby the pin operatively engages the spiral slot of the collet driver during locking of the locking device to the sleeve.

17. The medical lead anchor as in claim 15, wherein the collet has an internal grip.

18. The medical lead anchor as in claim 15, wherein the spiral slot of the collet driver extends to an arcuate slot section perpendicular to the centerline of the locking device.

19. The medical lead anchor as in claim 15, wherein the sleeve has bending members and protuberances thereon, and the locking device has recesses for the protuberances, the bending members bending as the locking device and the sleeve are rotated to move the protuberances into and out of the recesses, for releasably locking the locking device to the sleeve.

20. The medical lead anchor as in claim 15, wherein the collet has at least one slit.

21. A medical lead anchor for securing and repositioning a lead in the epidural space of the spinal cord comprising:

a sleeve having a plurality of eyelets, and a passage through the sleeve with a taper, a locking device including a collet, a collet driver, and a handle, and defining a centerline and a lead passage through the locking device, the collet having a plurality of slits, a tapered end and an internal grip, the collet driver having a spiral slot and sized to engage the tapered passage in the sleeve, and a pin on the sleeve located within the spiral slot, whereby when the lead is properly positioned in the epidural space, the sleeve is fitted on the lead through the tapered passage in the sleeve, the sleeve may be sutured to human tissue adjacent the epidural space using the plurality of eyelets, and, as the handle of the locking device is turned, the pin travels along the spiral slot of the collet driver and advances the collet through the passage in the sleeve, pinching the collet to a pre-determined tightness on the lead and securing the lead with the internal grip of the collet in the desired position.

* * * * *